(12) United States Patent
Schlaeper et al.

(10) Patent No.: US 8,632,485 B2
(45) Date of Patent: Jan. 21, 2014

(54) PATIENT TREATMENT AND MONITORING SYSTEMS AND METHODS

(75) Inventors: Christian Schlaeper, Concord, CA (US); Martin Crnkovich, Walnut Creek, CA (US); Jeffrey J. Sands, Celebration, FL (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 267 days.

(21) Appl. No.: 12/613,394

(22) Filed: Nov. 5, 2009

(65) Prior Publication Data

US 2011/0105979 A1  May 5, 2011

(51) Int. Cl.
*A61M 37/00* (2006.01)
*C02F 1/44* (2006.01)
*G06Q 50/00* (2012.01)

(52) U.S. Cl.
USPC ........ 604/4.01; 604/5.01; 604/6.09; 210/645; 210/739; 705/3

(58) Field of Classification Search
USPC .............. 604/4.01, 5.01, 5.04, 6.09; 210/645, 210/646, 739; 422/44; 700/11; 702/19; 715/33; 705/3
See application file for complete search history.

(56) References Cited

U.S. PATENT DOCUMENTS

| | | |
|---|---|---|
| 3,637,997 A | 1/1972 | Petersen |
| 4,245,244 A | 1/1981 | Lijewski et al. |
| 5,025,523 A | 6/1991 | Zappa et al. |
| 5,185,597 A | 2/1993 | Pappas et al. |
| 5,276,611 A | 1/1994 | Ghiraldi |
| 5,283,560 A | 2/1994 | Bartlett |
| 5,293,470 A | 3/1994 | Birch et al. |

(Continued)

FOREIGN PATENT DOCUMENTS

| | | |
|---|---|---|
| DE | 10049393 A1 | 4/2002 |
| EP | 1271386 A2 | 1/2003 |

(Continued)

OTHER PUBLICATIONS

[No Author] Dialysis data acquisition and management system: Finesse® Professional. Fresenius Medical Care. Product information sheet. 2002, 2 pages.

(Continued)

*Primary Examiner* — Leslie Deak
(74) *Attorney, Agent, or Firm* — Nutter McClennen & Fish LLP; David J. Powsner

(57) ABSTRACT

The invention provides apparatus and methods for home or other remote delivery of health care that gather subjective and objective measures of patient health and treatment, analyzing them (e.g., correlating them with one another and/or with norms) and reporting them to aid in on-going patient diagnosis and treatment (both on acute and chronic bases), as well as to aid physicians, nurses and other caregivers in decision support, monitoring treatment compliance, facilitating regulatory compliance, billing, and so forth. Thus, for example, in some aspects a health care delivery device comprising a medical treatment apparatus, such as a home hemodialysis or home peritoneal dialysis unit, that is coupled to a processor. The processor generates patient queries in connection with treatments rendered by the dialysis equipment (or other treatment apparatus). The queries are directed, at least in part, to subjective topics, such as the state of the patient's mental health and well being, quality of life, degrees of pain, views on success of therapy, and so forth. They are presented on an LCD screen or other output device coupled to the processor to elicit responses on a keyboard or other input device, also coupled to the processor.

17 Claims, 4 Drawing Sheets

(56) References Cited

U.S. PATENT DOCUMENTS

| | | | |
|---|---|---|---|
| 5,304,173 A | 4/1994 | Kittrell et al. |
| 5,345,250 A | 9/1994 | Inoue et al. |
| 5,367,316 A | 11/1994 | Ikezaki |
| 5,389,947 A | 2/1995 | Wood et al. |
| 5,396,281 A | 3/1995 | Maeda |
| 5,401,238 A | 3/1995 | Pirazzoli |
| 5,434,626 A | 7/1995 | Hayashi et al. |
| 5,690,813 A | 11/1997 | Coale |
| 5,781,442 A | 7/1998 | Engleson et al. |
| 5,798,752 A | 8/1998 | Buxton et al. |
| 5,838,291 A | 11/1998 | Ohshima et al. |
| 5,850,221 A | 12/1998 | Macrae et al. |
| 5,858,239 A | 1/1999 | Kenley et al. |
| 5,865,745 A | 2/1999 | Schmitt et al. |
| 5,900,859 A | 5/1999 | Takishita et al. |
| 5,903,211 A | 5/1999 | Flego et al. |
| 5,933,136 A | 8/1999 | Brown |
| 5,946,659 A | 8/1999 | Lancelot et al. |
| 6,057,826 A | 5/2000 | Gaultier et al. |
| 6,067,157 A | 5/2000 | Altendorf |
| 6,118,430 A | 9/2000 | Igari |
| 6,143,181 A | 11/2000 | Falkvall et al. |
| 6,146,523 A | 11/2000 | Kenley et al. |
| 6,151,581 A | 11/2000 | Kraftson et al. |
| 6,228,047 B1 | 5/2001 | Dadson et al. |
| 6,335,725 B1 | 1/2002 | Koh et al. |
| 6,335,761 B1 | 1/2002 | Glen et al. |
| 6,359,631 B2 | 3/2002 | DeLeeuw |
| 6,462,786 B1 | 10/2002 | Glen et al. |
| 6,469,695 B1 | 10/2002 | White |
| 6,493,002 B1 | 12/2002 | Christensen |
| 6,493,747 B2 | 12/2002 | Simmon et al. |
| 6,507,868 B2 | 1/2003 | Simmon et al. |
| 6,574,503 B2 | 6/2003 | Ferek-Petric |
| 6,684,379 B2 | 1/2004 | Skoll et al. |
| 6,736,789 B1 | 5/2004 | Spickermann |
| 6,738,052 B1 | 5/2004 | Manke et al. |
| 6,746,398 B2 | 6/2004 | Hervy et al. |
| 6,820,050 B2 | 11/2004 | Simmon et al. |
| 6,912,664 B2 | 6/2005 | Ranganathan et al. |
| 6,919,269 B2 | 7/2005 | Schneegans et al. |
| 6,982,727 B2 | 1/2006 | Baer et al. |
| 7,015,899 B2 | 3/2006 | Kim |
| 7,038,588 B2 | 5/2006 | Boone et al. |
| 7,044,927 B2 | 5/2006 | Mueller et al. |
| 7,088,343 B2 | 8/2006 | Smith et al. |
| 7,134,966 B1 | 11/2006 | Tice |
| 7,154,397 B2 | 12/2006 | Zerhusen et al. |
| 7,170,500 B2 | 1/2007 | Canova, Jr. |
| 7,185,282 B1 | 2/2007 | Naidoo et al. |
| 7,188,151 B2 | 3/2007 | Kumar et al. |
| 7,190,352 B2 | 3/2007 | Ling et al. |
| 7,215,991 B2 | 5/2007 | Besson et al. |
| 7,284,262 B1 | 10/2007 | Meric et al. |
| 7,336,187 B2 | 2/2008 | Hubbard, Jr. et al. |
| 7,351,340 B2 | 4/2008 | Connell et al. |
| 7,584,108 B2 | 9/2009 | Brown |
| 7,627,334 B2 | 12/2009 | Cohen et al. |
| 7,685,005 B2 | 3/2010 | Riff et al. |
| 7,801,746 B2 | 9/2010 | Moll et al. |
| 8,182,440 B2 | 5/2012 | Cruz et al. |
| 2001/0005115 A1 | 6/2001 | Busio et al. |
| 2001/0011036 A1 | 8/2001 | Miyamoto et al. |
| 2001/0016056 A1 | 8/2001 | Westphal et al. |
| 2001/0034614 A1 | 10/2001 | Fletcher-Haynes et al. |
| 2001/0045395 A1 | 11/2001 | Kitaevich et al. |
| 2001/0056226 A1 | 12/2001 | Zodnik et al. |
| 2002/0032385 A1 | 3/2002 | Raymond et al. |
| 2002/0035637 A1 | 3/2002 | Simmon et al. |
| 2002/0082728 A1 | 6/2002 | Mueller et al. |
| 2002/0107449 A1 | 8/2002 | Roeher |
| 2002/0163178 A1 | 11/2002 | Williams |
| 2002/0198473 A1 | 12/2002 | Kumar et al. |
| 2003/0001743 A1 | 1/2003 | Menard |
| 2003/0018395 A1 | 1/2003 | Crnkovich et al. |
| 2003/0069481 A1 | 4/2003 | Hervy et al. |
| 2003/0083901 A1 | 5/2003 | Bosch et al. |
| 2003/0141981 A1 | 7/2003 | Bui et al. |
| 2003/0197690 A1 | 10/2003 | Zimenkov |
| 2003/0220607 A1 | 11/2003 | Busby et al. |
| 2004/0021673 A1 | 2/2004 | Alessi et al. |
| 2004/0111293 A1 | 6/2004 | Firanek et al. |
| 2004/0111294 A1 | 6/2004 | McNally et al. |
| 2004/0176984 A1 | 9/2004 | White et al. |
| 2004/0193448 A1 | 9/2004 | Woodbridge et al. |
| 2004/0220832 A1 | 11/2004 | Moll et al. |
| 2004/0260478 A1 | 12/2004 | Schwamm |
| 2004/0261037 A1 | 12/2004 | Ording et al. |
| 2005/0021369 A1 | 1/2005 | Cohen et al. |
| 2005/0081164 A1 | 4/2005 | Hama et al. |
| 2005/0139515 A1 | 6/2005 | Gu et al. |
| 2005/0213425 A1 | 9/2005 | Wang et al. |
| 2006/0058603 A1 | 3/2006 | Dave et al. |
| 2006/0062238 A1 | 3/2006 | Mahendran et al. |
| 2006/0066581 A1 | 3/2006 | Lyon et al. |
| 2006/0176403 A1 | 8/2006 | Gritton et al. |
| 2006/0190297 A1 | 8/2006 | Glass et al. |
| 2006/0231108 A1 | 10/2006 | Novatzky et al. |
| 2007/0020341 A1 | 1/2007 | Miyata |
| 2007/0040787 A1 | 2/2007 | Saha |
| 2007/0046596 A1 | 3/2007 | Sakakibara et al. |
| 2007/0078878 A1 | 4/2007 | Knable |
| 2007/0112603 A1 | 5/2007 | Kauthen et al. |
| 2007/0125709 A1 | 6/2007 | Nigam |
| 2007/0130287 A1 | 6/2007 | Kumar et al. |
| 2007/0168229 A1 | 7/2007 | Kim |
| 2007/0223877 A1 | 9/2007 | Kuno |
| 2008/0015487 A1 | 1/2008 | Szamosfalvi et al. |
| 2008/0097283 A1 | 4/2008 | Plahey |
| 2008/0097550 A1 | 4/2008 | Dicks et al. |
| 2008/0154177 A1 | 6/2008 | Moubayed et al. |
| 2008/0268413 A1 | 10/2008 | Leichner |
| 2008/0275721 A1 | 11/2008 | Nagai et al. |
| 2009/0008331 A1 | 1/2009 | Wilt et al. |
| 2009/0037216 A1 | 2/2009 | Bluemler et al. |
| 2009/0076338 A1 | 3/2009 | Zdeblick et al. |
| 2009/0076856 A1 | 3/2009 | Darby et al. |
| 2010/0137693 A1 | 6/2010 | Porras et al. |

FOREIGN PATENT DOCUMENTS

| | | |
|---|---|---|
| EP | 2043014 A1 | 4/2009 |
| JP | 2003006331 A | 1/2003 |
| JP | 2008284229 A | 11/2008 |
| KR | 2001-091801 A | 10/2001 |
| WO | WO-9628086 | 9/1996 |
| WO | WO-0207591 | 1/2002 |
| WO | WO-2004070995 A2 | 8/2004 |
| WO | WO-2006020862 A2 | 2/2006 |
| WO | WO-2006122325 | 11/2006 |
| WO | WO-2007033600 A1 | 3/2007 |
| WO | WO-2007035696 | 3/2007 |
| WO | WO-2007/040963 | 4/2007 |
| WO | WO-2007/040975 | 4/2007 |
| WO | WO-2007/044877 | 4/2007 |
| WO | WO-2007038147 | 4/2007 |
| WO | WO-2007/053683 | 5/2007 |
| WO | WO-2007049163 A2 | 5/2007 |
| WO | WO-2007049253 A2 | 5/2007 |
| WO | WO-2007120904 A2 | 10/2007 |
| WO | WO-2007126360 A1 | 11/2007 |
| WO | WO-2008008281 A2 | 1/2008 |
| WO | WO-2009002620 A1 | 12/2008 |

OTHER PUBLICATIONS

[No Author] Dialysis data management system FinProDB: Finesse® Professional Database. Fresenius Medical Care. Product information sheet. 2004, 2 pages.

[No Author] Exalis: Dialysis data management tool. Gambro Lundia AB. Product information sheet. Jun. 2002, 8 pages.

[No Author] Finesse®. Fresenius Medical Care. Retrieved Jun. 17, 2009 from http://fmc.intra.fresenius.de. 2008, 2 pages.

(56) References Cited

OTHER PUBLICATIONS

[No Author] Finesse® HomeHemo Dialysis (TI 1025 e, v2.01). Medvision AG. Product information sheet. 2004, 6 pages.

[No Author] Therapy Data Management System: Data acquisition, data management and quality assurance as an integrated solution. Fresenius Medical Care. Product information sheet. 2007, 12 pages.

International Search Report issued Jul. 23, 2007, for Application No. PCT/US2006/42650 (11 pages).

"Interactive Hospital Menus Go Prime Time" Internet Article, Dietary Manager Magazine, (Online) Apr. 2007, pp. 29-31, XP002505453, Retrieved from the internet: http://www.dmaonline.org/Publications/articles/2007_04_Interactive.pdf.

"PatientLife:)System TM . . . your comprejensive solution for patient-sentered care," Internet Article, Brouchure, Getwellnetwork, Inc., (Online) Mar. 18, 2006, pp. 1-6, XP002505452, http://web.archive.org/web/20060318175409/http://www.getwellnetwork.com/pdfs/GWNProductBrochure.pdf.

European Search Report, EP Application No. 08164693.7, Mailed Dec. 10, 2008.

Intel 510k Summary, Jun. 27, 2008.

Nakamoto, Telemedicine System for Patients on Continuous Ambulatory Peritoneal Dialysis, Peritoneal Dialysis International, vol. 27, 2007.

NHS Lothian Implements Intels Personal Health System to Manage Patients with Chronic Conditions, Intel, Feb. 24, 2009.

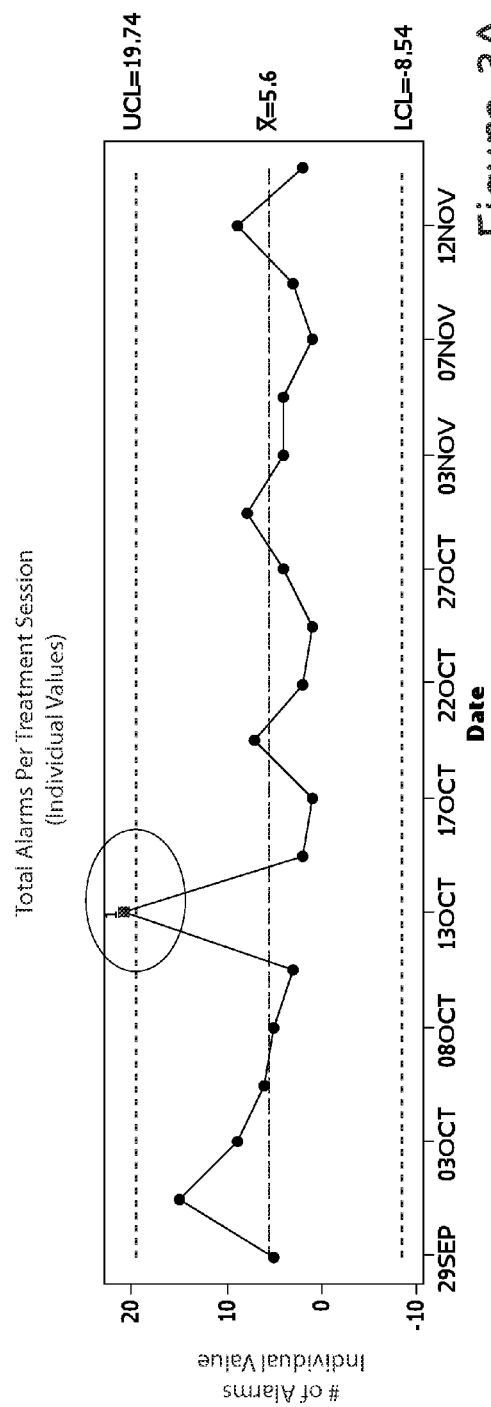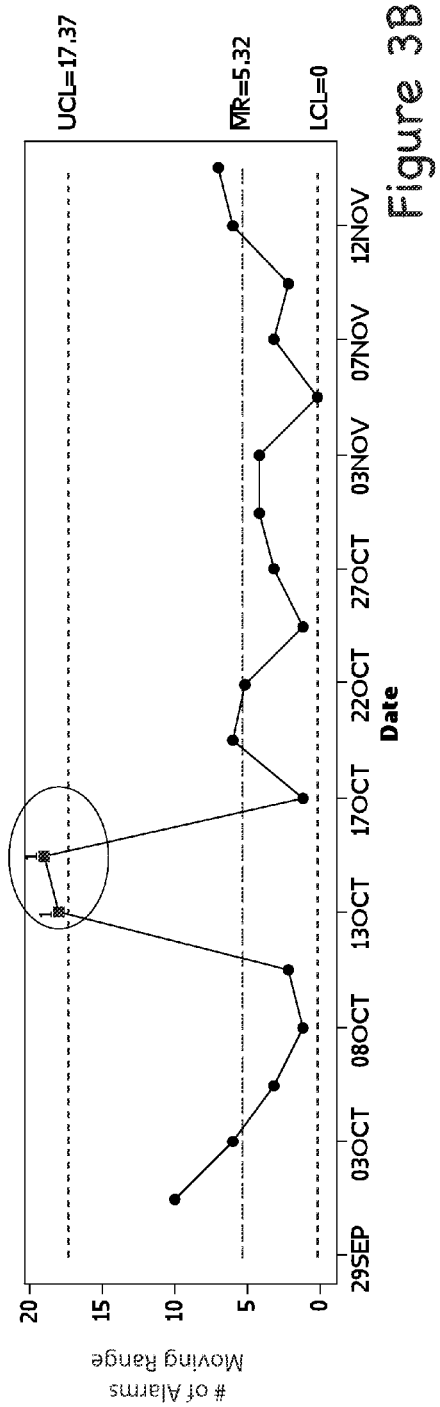

Average Number of Alarms Per Treatment Session By Category

| Patient | Air | AP | BF | Bld | Con | DF | Temp | TMP | VP | Total | Comments |
|---|---|---|---|---|---|---|---|---|---|---|---|
| 1 | 0.25 | 0.50 | 0.50 | 0.00 | 0.50 | 0.25 | 0.00 | 0.25 | 0.75 | 3.00 | Needs training, Water pressure pr |
| 2 | 0.00 | 0.57 | 0.29 | 0.00 | 0.29 | 0.00 | 0.00 | 0.00 | 0.43 | 1.57 | |
| 3 | 0.08 | 0.38 | 0.08 | 0.00 | 0.00 | 0.00 | 0.00 | 0.15 | 0.23 | 0.92 | |
| 4 | 0.00 | 0.05 | 0.00 | 0.00 | 0.30 | 0.00 | 0.00 | 0.00 | 0.15 | 0.50 | |
| 5 | 0.00 | 0.43 | 0.07 | 0.00 | 0.50 | 0.00 | 0.00 | 0.00 | 0.14 | 1.14 | |
| 6 | 0.00 | 0.14 | 0.00 | 0.00 | 0.14 | 0.00 | 0.00 | 0.00 | 0.29 | 0.57 | |
| 7 | 0.00 | 0.25 | 0.00 | 0.00 | 0.50 | 0.00 | 0.00 | 0.00 | 0.50 | 1.25 | |
| 8 | 0.20 | 0.40 | 0.20 | 0.00 | 0.00 | 0.00 | 0.00 | 0.20 | 0.20 | 1.20 | |
| 9 | 0.29 | 0.43 | 0.00 | 0.00 | 0.00 | 0.00 | 0.00 | 0.14 | 0.14 | 1.00 | |
| 10 | 0.05 | 0.21 | 0.11 | 0.00 | 0.00 | 0.05 | 0.05 | 0.05 | 0.16 | 0.68 | |
| 11 | 0.00 | 0.40 | 0.20 | 0.00 | 0.00 | 0.00 | 0.00 | 0.00 | 0.20 | 0.80 | |
| 12 | 0.00 | 0.50 | 0.17 | 0.00 | 0.00 | 0.00 | 0.83 | 0.00 | 0.33 | 1.83 | May need tempering valve |
| 13 | 0.07 | 0.21 | 0.00 | 0.00 | 0.00 | 0.00 | 0.00 | 0.00 | 0.07 | 0.36 | |
| 14 | 0.10 | 0.30 | 0.00 | 0.00 | 0.10 | 0.00 | 0.00 | 0.10 | 0.60 | 1.20 | |
| 15 | 0.00 | 0.00 | 0.10 | 0.00 | 0.80 | 0.00 | 0.00 | 0.00 | 0.00 | 0.90 | Recurrent conductivity alarms |
| 16 | 0.00 | 0.50 | 0.00 | 0.00 | 1.00 | 0.00 | 0.00 | 0.50 | 0.50 | 2.50 | Recurrent conductivity alarms |
| 17 | 0.00 | 0.17 | 0.00 | 0.00 | 0.50 | 0.00 | 0.00 | 0.00 | 0.00 | 0.67 | |
| 18 | 0.00 | 0.00 | 0.00 | 0.00 | 1.00 | 0.00 | 0.00 | 0.00 | 0.00 | 1.00 | |
| 19 | 0.00 | 0.00 | 0.00 | 0.00 | 0.00 | 0.00 | 0.00 | 0.33 | 0.00 | 0.33 | |
| 20 | 0.20 | 0.40 | 0.20 | 0.00 | 0.20 | 0.00 | 0.00 | 0.60 | 0.60 | 2.20 | |
| 21 | 0.25 | 0.15 | 0.05 | 0.00 | 0.05 | 0.00 | 0.00 | 0.20 | 0.50 | 1.20 | |
| 22 | 0.00 | 0.00 | 0.00 | 0.00 | 0.08 | 0.00 | 0.00 | 0.00 | 0.08 | 0.15 | |
| 23 | 0.27 | 0.20 | 0.07 | 0.00 | 0.73 | 0.07 | 0.00 | 0.40 | 0.33 | 2.07 | Recurrent conductivity alarms |
| 24 | 0.00 | 0.59 | 0.29 | 0.00 | 0.94 | 0.06 | 0.00 | 0.24 | 0.35 | 2.47 | Recurrent conductivity alarms |
| 25 | 0.00 | 0.50 | 0.00 | 0.00 | 0.13 | 0.00 | 0.00 | 0.00 | 0.25 | 0.88 | |
| 26 | 0.30 | 0.30 | 0.10 | 0.00 | 0.60 | 0.00 | 0.00 | 0.00 | 0.10 | 1.40 | |
| 27 | 0.13 | 0.63 | 0.13 | 0.00 | 0.13 | 0.00 | 0.00 | 0.25 | 0.50 | 1.75 | |
| | Air | AP | BF | Bld | Con | DF | Temp | TMP | VP | Total | |
| Facility Total | 0.08 | 0.28 | 0.08 | 0.00 | 0.29 | 0.015 | 0.023 | 0.11 | 0.25 | 1.15 | |
| Reference standard | 0.06 | 0.38 | 0.10 | 0.01 | 0.04 | 0.002 | 0.006 | 0.09 | 0.28 | 0.96 | |
| Ratio Facility/Stand | 152% | 75% | 88% | 0% | 686% | 831% | 415% | 114% | 91% | 119% | |

KEY

IC – in center
AIR – air detector alarm
AP – arterial pressure
BF – blod flow
BLD – bood leaked detector
CON – conductvity
DF – dialysate flow
Temp – temperature
TMP – transmemberante pressure
VP – venus pressure
total – total alarms
▨ - high alarm rate
▦ - medium alarm rate
☐ - low alarm rate

Figure 4

PATIENT TREATMENT AND MONITORING SYSTEMS AND METHODS

BACKGROUND OF THE INVENTION

The invention relates to apparatus and methods for medical treatment. It has application, by way of non-limiting example, in the delivery of dialysis care in the home.

Dialysis is an important treatment regimen for a variety of chronic diseases. To meet the need for regular care, patients typically travel to hospitals or dialysis centers that are designed for efficient and routine therapy. Typically, a nurse or patient care technician oversees the treatment sessions and records patient information, such as patient vitals, treatment details, and billing information. The nurse or care technician can also assess the patient's health and, if necessary, make a referral to his or her regular physician (or, if necessary, to an emergency physician) for additional medical attention.

With the advent of more affordable equipment, home dialysis is increasingly an option for many dialysis patients, who find it offers them greater privacy, flexibility of scheduling and overall comfort. Home provision of hemodialysis can also be advantageous to health care providers since it does not require the nursing, equipment and space overhead of standard in-center care. Medicare/Medicaid and other insurers stand to benefit, too, since home hemodialysis tends to lower coverage costs over the long term.

The decision to place a patient on home hemodialysis (HHD) is not necessarily an easy one, however. The demands of a hemodialysis regime, even one administered in the home, are such that HHD programs suffer a high dropout rate as patients revert to in-center dialysis. These dropouts are not necessarily for medical reasons but, rather, are often due to the mental and/or physical demands HHD care places on patients and their partners. Considering the costs of providing patient training, the expenses of adjustment of the infrastructure at the patient's home, cost for installation of the equipment and delivery charges, patients that drop out of HHD programs create an economic burden on the health care system.

Even for those patients on a course of HHD therapy, full compliance with the regimen can be difficult. This is true, for example, with respect to administration of medications taken as part of the regimen. Erythropoietin, a drug commonly administered to hemodialysis patients to prevent anemia, is one example. Dosages of this expensive drug can be reduced, if it administered subcutaneously. That can be more painful, however, leading HHD patients to skip doses. This not only adversely affects treatment outcome but may raise the specter of insurance fraud—since, unless the patients admit they are under-dosing, care providers are likely to dispense and seek reimbursement for monthly complements of EPO, regardless of whether patients have used them.

An additional consideration in the decision to place a patient on HHD is that of patient monitoring. HHD therapy affords fewer opportunities to assess patient health, well-being and treatment compliance. Care givers typically have that opportunity only when HHD patients visit their local dialysis clinic for monthly evaluation—and, then, only to the extent that the success of treatment can be determined from routine testing and from patient reporting. Significantly, although HHD equipment may record limited patient information (such as date/time of treatment, blood pressure and pulse), it does not afford the care giver insight into adverse events that occur during actual HHD treatment sessions, such as dizziness, vomiting and cramps. Moreover, while the prior art does suggest that there has been some effort to collect in a central databases even the limited patient data acquired by HHD equipment, this has not been perceived by care providers as a suitable substitute for in-center visits.

In view of the foregoing an object of the invention is to provide improved medical care systems and methods. A more particular object is to provide such systems and methods as are adapted for patient treatment and monitoring.

A further object of the invention is to provide such systems and methods as are adapted for use in home (or other remote) health delivery.

A still further object of the invention is to provide such systems and methods as are adapted for use in hemodialysis and peritoneal dialysis treatment.

SUMMARY OF THE INVENTION

The foregoing are among the objects attained by the invention, which provides apparatus and methods for delivery of health care that collect subjective and objective measures of patient health and treatment, analyzing them (e.g., correlating them with one another, with prior such information and/or with norms) and reporting them to aid in on-going patient diagnosis and treatment (both on acute and chronic bases), as well as to aid physicians, nurses and other caregivers in decision support, monitoring treatment compliance, facilitating regulatory compliance, billing, and so forth. Advantages of the system are, among others, that it helps ensure that the patient is doing as expected (e.g., in terms of physical health, mental health and well-being, and/or treatment compliance), allowing care providers to readily monitor and document (or otherwise report on) the patient's treatment and response, providing alerts or other warnings when those are not proceeding as expected.

Thus, for example, in some aspects, the invention provides a health care delivery device comprising a medical treatment apparatus, such as a home hemodialysis or home peritoneal dialysis unit, that is coupled to a processor. The processor generates patient queries in connection with treatments rendered by dialysis equipment (or other treatment apparatus). The queries are directed, at least in part, to subjective topics, such as the state of the patient's mental health and well being, quality of life, degrees of pain, views on success of therapy, and so forth. They are presented on an LCD screen or other output device coupled to the processor to elicit responses on a keyboard or other input device, also coupled to the processor.

Further aspects of the invention provide a health care delivery device, for example, as described above, that includes communications logic, e.g., hardware and/or software operating in conjunction with the processor, that transmits the patient's query responses to a health care provider, e.g., a nurse or patient care technician at a dialysis center. Those responses can transmitted in connection with treatments rendered by the dialysis equipment (or other treatment apparatus), e.g., at or around the time of completion of each treatment session.

In related aspects of the invention, a health care delivery device, for example, as described above, can include a memory or other store for patient responses. That store can operate in connection with the communications logic, e.g., retaining the responses while awaiting transmission to the health care provider.

Further aspects of the invention provide a health care delivery device, for example, as described above, wherein the communications logic transmits text or other messages input by the patient (e.g., via the input device) to the health care provider. The messages can be, for example, questions by the patient regarding his or her immediate or long-term treatment. In related aspects of the invention, the communications logic of such a health care delivery device can accept messages transmitted from the provider and can present those messages on the output device. These can be, for example, responses to the patient's questions, suggestions on treatment, words of encouragement, and so forth.

Still further aspects of the invention provide a health care delivery device, for example, as described above, that includes one or more physiometric sensors that take readings, e.g., of patient temperature, blood pressure, other vital signs, and so forth, in connection with treatments rendered by the dialysis equipment (or other treatment apparatus). The communications logic can transmit those readings to the health care provider, e.g., along with the patient's responses to the queries for the corresponding treatment session.

In related aspects of the invention, a health care delivery device, for example, as described above, includes one or more sensors that sense operating conditions of any of the health device and the medical treatment apparatus. The communications logic can transmit those readings to the health care provider, e.g., along with the patient's responses to the queries and/or physiometric readings for the corresponding treatment session.

In further related aspects of the invention, a health care delivery device, for example, as described above, includes one or more one or more monitors that signal alerts or alarms (terms which are used interchangeably herein) in response to any of (i) selected patient patient physiometric characteristics, e.g., pulse, blood pressure and/or other vital sign readings over designated values, etc., and (ii) selected operating conditions of any of the health device and the medical treatment apparatus, e.g., diagnostic warnings, power surges, and so forth. As above, the communications logic can transmit those alerts to the health care provider, e.g., along with the patient's responses and/or physiometric readings.

Still other aspects of the invention provide a health care delivery system that includes a health care delivery device, for example, as described above, that is coupled to a digital data processing system, e.g., by way of the Internet, a cellular phone network, or other arrangement of wireless and/or wired network media. In a system according to this aspect of the invention, the health care delivery device can be disposed, for example, in a patient's home and the digital data processing system can be disposed, for example, in a hospital, dialysis center or other central location. The communication system, according to these aspects of the invention, transmits patient responses, physiometric readings, operating conditions and/or alerts to the remote digital data processing system, e.g., in connection with treatments rendered by the dialysis equipment (or other treatment apparatus) or otherwise.

In related aspects of the invention, the digital data processing system of a health care delivery system, e.g., as described above, analyzes patient responses, physiometric readings, operating conditions and/or alerts received from the health care delivery device and, for example, correlates them with (i) each other, (ii) prior responses, readings, conditions, alerts from the device and/or other information for the patient (e.g., from medical records), (iii) expected responses, readings, conditions and/or alerts, e.g., based on empirical, normative or other standards, and/or (iv) so forth, in order to aid the health care provider in on-going patient diagnosis and treatment (both on acute and chronic bases), decision support, monitoring treatment compliance, facilitating regulatory compliance, billing, and so forth.

In other related aspects of the invention, the digital data processing system of a health care delivery system, e.g., as described above, includes reporting functionality that reports patient responses, physiometric readings, operating conditions and/or alerts received from the health care delivery device. These can be on a per-session basis or over selected periods of time, e.g., per day, per week, etc. Alternatively and/or in addition, this functionality can report results of the aforementioned correlation(s), e.g., indicating whether the responses, readings, conditions and/or alerts show unexpected and/or undesirable indications.

By way of non-limiting example, the reporting functionality can report treatment times, medication dosages and times, alarms, and so forth. This can be used by the health care provider in providing acute and/or chronic care. It can be used, alternatively or in addition, for regulatory, billing or other such purposes. Selected portions of these reports, for example, can be automatically transmitted to the physician, nurse and other caregivers, as well as, for example, to the patient (e.g., via e-mail, messaging transmitted from the digital data processor to the health care delivery device, etc.), the insurer and/or others.

In other aspects of the invention, one or more of the aforementioned functions of the digital data processor can be carried out, instead or in addition, by the health care delivery device. Thus, for example, the processor executing on that device can analyze patient responses, physiometric readings, operating conditions and/or alerts and correlate them with (i) each other, (ii) prior responses, readings, conditions, alerts from the device and/or other information for the patient (e.g., from medical records), (iii) expected responses, readings, conditions and/or alerts, e.g., based on empirical, normative or other standards, and/or (iv) so forth. While the results of such analysis can be transmitted to the remote digital data processing system, e.g., for reporting to the health care provider, those results can be also be used to generate more urgent messages to the patient and/or his health care provider.

Other aspects of the invention provide a health care delivery system as described above in which the health care delivery device and the digital data processing system are located at the same facility (e.g., in a hospital, dialysis center or other central location) and/or in the same department, floor, ward and/or room of such a facility.

Still further aspects of the invention provide methods paralleling operation of the health care device, system, and components thereof, discussed above. By way of non-limiting example, one such method includes delivering medical treatment to a patient via a medical treatment apparatus, subjectively querying the patient via a health care treatment device associated with the medical treatment apparatus, accepting patient responses to those subjective queries, and transmitting the patient responses to a remote health care provider.

These and other aspects of the invention are evident in the drawings and in the text that follows.

BRIEF DESCRIPTION OF THE DRAWINGS

A more complete understanding of the invention may be attained by reference to the drawings, in which:

FIGS. 3-4 depict examples of reports of the type generated by a health care delivery system of FIG. 1.

DETAILED DESCRIPTION OF THE ILLUSTRATED EMBODIMENT

Architecture

Figure 1:
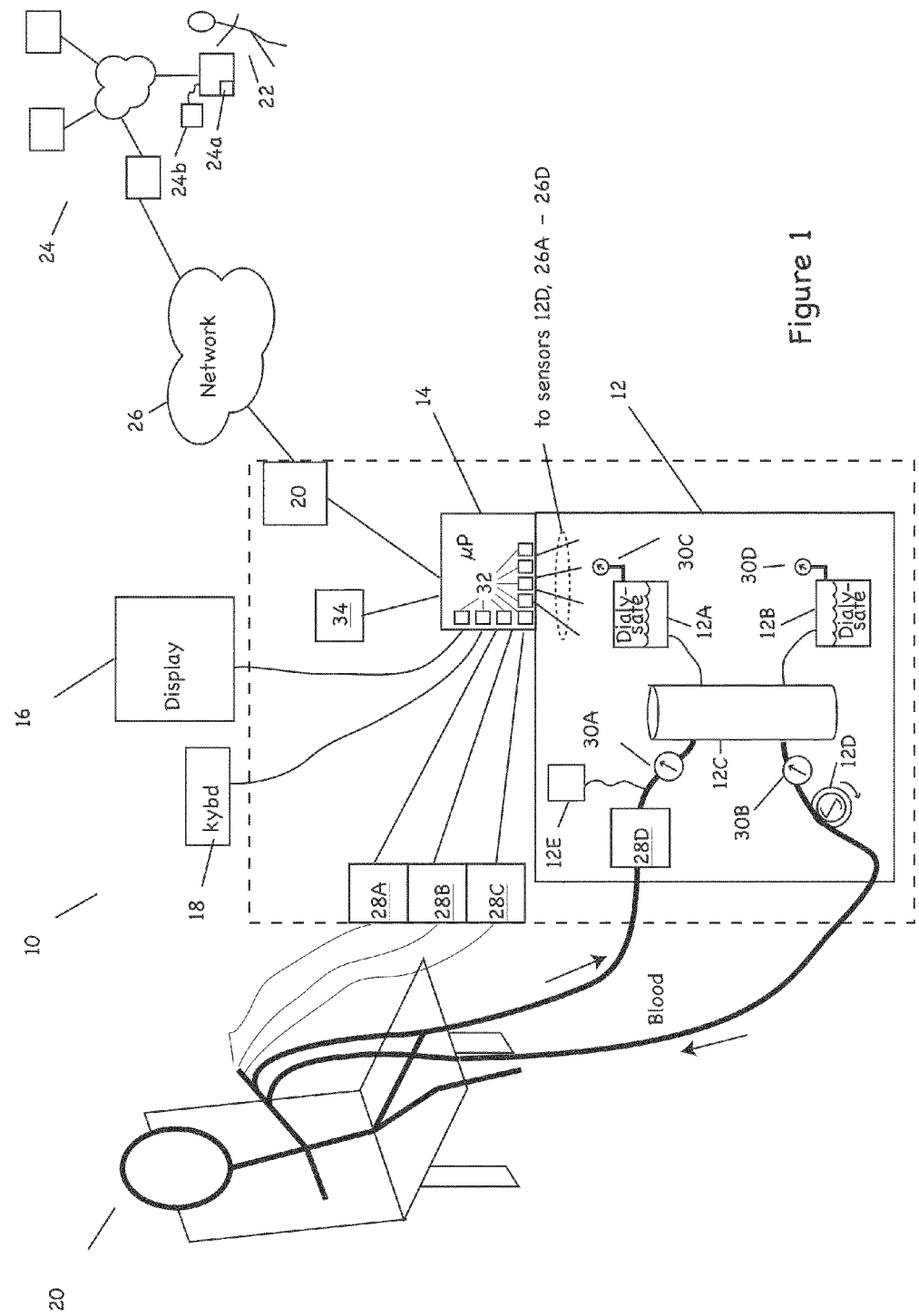
FIG. 1 depicts examples of a health care delivery device and system according to the invention.

FIG. 1 depicts examples of a health care delivery device and system according to the invention. Illustrated device 10 comprises a medical treatment apparatus 12, a processor 14, an output device 16 and an input device 18, all coupled as shown.

Illustrated medical treatment apparatus comprises a dialysis unit and, more particularly, a hemodialysis unit of the type commercially available or otherwise known in the art for such purpose, e.g., including, for example, fresh and spent dialysate containers 12A, 12B, filter/dialyzer 12C, pump 12D, supplemental infusate supply 12E (e.g., for heparin and/or other medications), and so forth, as adapted in accord with the teachings hereof. The illustrated medical treatment apparatus 12 is, moreover, of the type adapted for use in the home or other locale remote for a dialysis center, hospital or other central treatment center. Alternatively, or in addition, the apparatus 12 may be adapted for use in such a dialysis center, hospital or other treatment center. This may, for example, at a location in such a center remote from a physician, nurse, patient care technician or other health care provider—or it may be nearby such a provider. In other embodiments apparatus 12 may comprise a peritoneal dialysis machine or other medical treatment apparatus of the type known in the art or otherwise, again, as adapted in accord with the teachings hereof.

Processor 14 comprises a microprocessor or other processing unit of type commercially available or otherwise known in the art, as adapted in accord with the teachings hereof. The processor 14 may be integral to medical treatment apparatus 12 or it may separate therefrom, albeit coupled for communication therewith. Illustrated processor 14 is coupled with liquid crystal display (LCD) or other output device 16, which may be of the type commercially available in the marketplace or otherwise known in the art, as adapted in accord with the teachings hereof. Processor 14 is also coupled with keyboard or other input device 18 (e.g., mouse, touch-screen, touchpad, etc.) which, too, may be of the type commercially available in the marketplace or otherwise known in the art, again, as adapted in accord with the teachings hereof. The LCD 16 (and/or other output device) and/or keyboard 18 (and/or other input device) may be integral to medical treatment apparatus 12 or separate therefrom. Alternatively, or in addition, LCD 16 and/or keyboard 18 may be cohoused with processor 14 or separate therefrom, as well as from one another.

Processor 14 is coupled with network interface 20 to support communications with a health care provider 22, e.g., a physician, nurse or patient care technician, via digital data processing system 24 and network media 26. That media 26 may comprise IP, telephone and/or other networks of the type known in the art—wired, wireless and/or otherwise. Network interface 20 comprises a modem, network interface card and/or other functionality of the type commercially available in the marketplace or otherwise known in the art suitable for supporting communications over network 26, as adapted in accord with the teachings hereof. Examples include cable modems, cellular telephone modems, USB modems, Ethernet cards, and combinations thereof, just to name a few. It will be appreciated that some of that functionality for supporting communications with care provider 22 via digital data processor 24 and network media 26 may reside on processor 14, as in the case, for example, of operating system drivers, network protocol stacks, and so forth. Together, this functionality (i.e., hardware and/or software) is referred to, here, as "communications logic."

Processor 14 is also coupled with sensors 28 that take biometric readings of the patient 20. These "physiometric sensors," as they are referred to herein, can include blood pressure sensors, temperature sensors, and so forth. In the illustrated embodiment they are of the type commercially available in the marketplace or otherwise known in the art, as adapted in accord with the teachings hereof. Those sensors may be integral to apparatus 12, processor 14 and/or co-housed with device 10, or otherwise. In the illustrated embodiment, the sensors include a pulse sensor 28A, a blood pressure sensor 28B, a temperature sensor 28C and a electrochemical sensor 28D (e.g., for sensing blood urea levels, ammonia levels, and so forth). Sensors 28A-28C are shown coupled to the patient, while sensor 28D is coupled in the blood fluid-flow path of apparatus 12. Other embodiments of the invention may include a greater or fewer number of such sensors, coupled to the patient, the flow-path of apparatus 12, etc., as shown or in other ways known in the art, as adapted in accord with the teachings hereof.

Processor 14 is also coupled to sensors 30 that sense operating conditions of the device 10, apparatus 12, and/or components thereof. These can include sensors that measure the rates of fluid flow, fluid temperature, level, and composition, power conditions, maintenance status and so forth, all by way of non-limiting example. In the illustrated embodiment they are of the type commercially available in the marketplace or otherwise known in the art, as adapted in accord with the teachings hereof. Those sensors may be integral to apparatus 12, processor 14 and/or co-housed with device 10, or otherwise. In the illustrated embodiment, the sensors include an inflow blood flow-rate or pressure sensor 30A, and outflow blood flow-rate or pressure sensor 30B, fresh dialysate level sensor 30C, spent dialysate level sensor 30D. An additional sensor (not shown) can, by way of non-limiting example, sense levels or dosings from supplemental infusate supply 12E. In other embodiments, other operational sensors of the type suggested above are provided instead or in addition to those shown in the drawing and/or discussed here.

Processor 14 can include monitoring logic, here, represented by modules 32, that monitor operational states of device 10 and/or apparatus 12, as well as detect alert or alarm (terms which are used interchangeably herein) conditions, e.g., as reported directly from components of device 10 and/or apparatus 12 and/or when readings from the physiometric sensors 28 and/or operational sensors 32 fall outside of selected ranges. That monitoring logic can also, by way of non-limiting example, monitor when and for how long the various sensor readings, for example, are outside those ranges.

Thus, for example, the monitoring logic 32 can detect the incidence and duration of systolic blood pressure readings below physician- (or other care provider-) defined levels, as well as changes (deltas) in blood pressure greater than such levels. By way of further example, the monitoring logic can detect when medications are administered and in what quantity. By way of still further example, the monitoring logic can detect when treatment sessions are initiated and how long they are run; the incidence and duration of "door ajar" alerts, "filter replacment" alerts, "dialysate replacement" alerts, and/or other alerts or conditions reflecting whether proper and efficient care is being delivered to the patient 20, and so forth. Though illustrated here has modules (i.e., software and/or hardware) executing on/forming part of processor 14, in other embodiments, monitoring logic 32 can be form part of apparatus 12 and/or may be co-housed with device 10, or otherwise.

Processor 14 is also coupled, in the illustrated embodiment, with a storage device 34, such as a disk drive, memory stick and/or other medium, removeable or otherwise.

Digital data processing system 24 comprises one or more cell phones, smart phones, personal digital assistants, computers, or other devices suitable for communicating with device 10 via network 26 to receive patient query responses, phyisometric sensor readings, operational sensor readings and/or alerts of the type described above. In the illustrated embodiment, the system 24 is remote from device 10 and comprises a computer system of the type commonly available in a hospital, dialysis center or other central location of the type that employs or otherwise physicians, nurses, patient care technicians or other health care providers to oversee treatment of patients 20, all as adapted in accord with the teachings hereof. In other embodiments, the system 24 is located with the device 10 at the same facility (e.g., in a hospital, dialysis center or other central location) and/or in the same department, floor, ward and/or room of such a facility, by way of non-limiting example, and coupled therewith by way of a bus, network or other media, or combination thereof, wired or wireless, dedicated, shared or otherwise.

The illustrated system 24 also includes an analysis/reporting module 24A, implemented in software on one or more of the computers or other computational devices making up that system, that analyzes and/or reports the information collected and transmitted by device 10 in accord with the teachings hereof to aid in on-going patient diagnosis and treatment, as well as to aid physicians, nurses and other caregivers in diagnostics, decision support, monitoring treatment compliance, billing, and so forth. The system 24 also includes an LCD display or other output unit 24B of the type commercially available in the marketplace or otherwise known in the art (as adapted in accord with the teachings hereof) for presenting results generated by module 24A.

Operation

Figure 2:
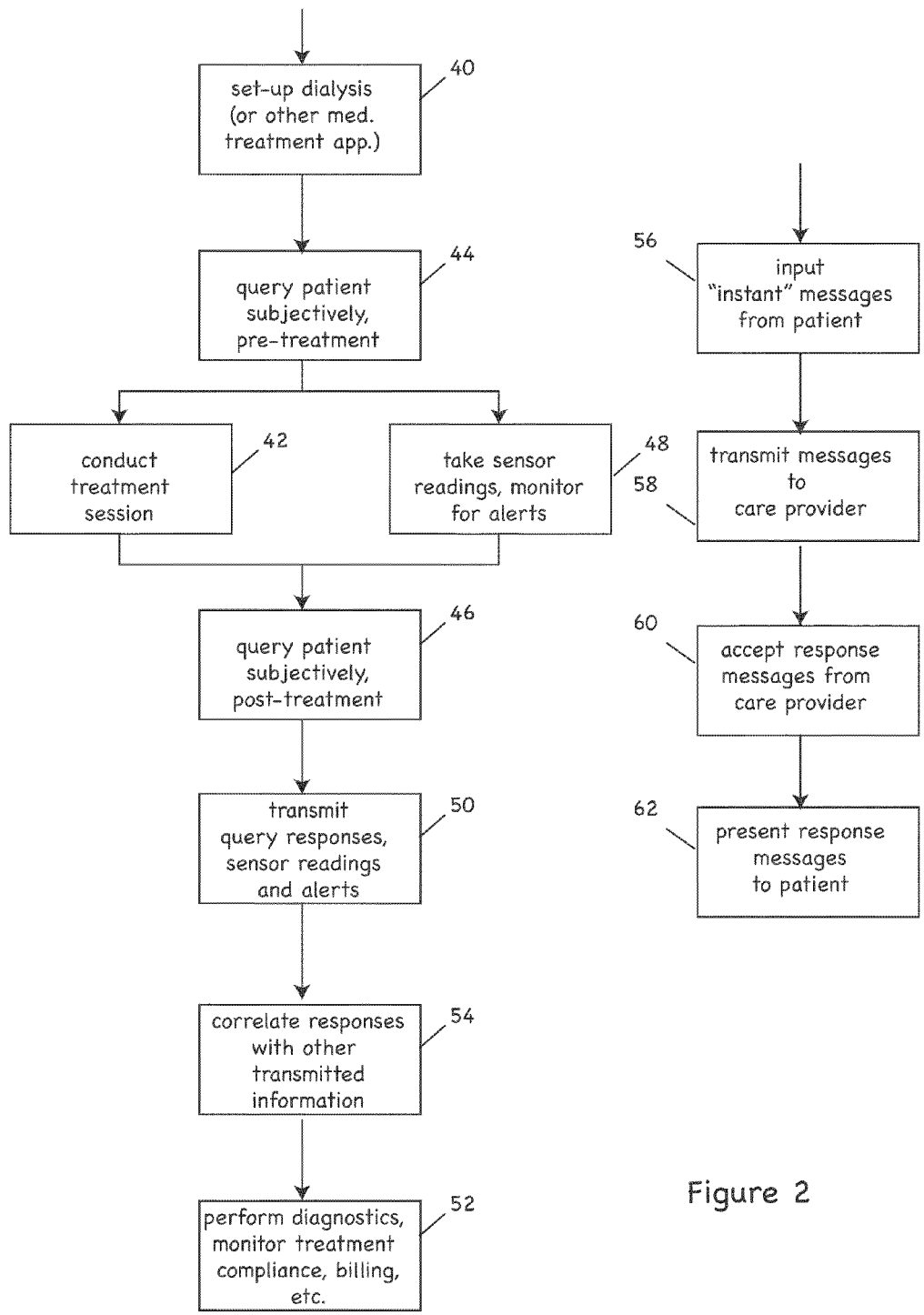
FIG. 2 depicts a method for operating a health care delivery device and system of FIG. 1.

FIG. 2 depicts operation of the system of FIG. 1 according to one practice of the invention. In step 40, apparatus 12 and sensors 28 are coupled to patient 20 and otherwise set-up for treatment delivery in the conventional manner known in the art (as adapted in accord with the teachings hereof).

In step 42, treatment is administered in the conventional manner known in the art, as adapted in accord with the teachings hereof. In connection with at least selected treatment sessions (e.g., every session, every other session, one session per week, or so forth), processor 14 generates queries to the patient 20. The queries can directed to, by way of non-limiting example, subjective topics, such as the patient's perception of his or her own mental health and well being, quality of life, degrees of pain, views on success of therapy, and so forth. The queries may include questions with yes/no answers, questions with a numeric grading, questions with a numeric value, and/or open-ended questions, etc. By way of example, queries designed to uncover depression (which has a correlation with patient morbidity and mortality) may include general questions regarding the emotional status of the patient and the quality of life and screens for depression. These may be questions to which the patient 20 responds with ratings, e.g., with values from one to five. The queries are not limited to subject topics and may include, for example, questions about the patient's eating habits, whether he/she is taking prescribed treatment medications and, if so, when and in what doses, and so forth.

In some embodiments, the processor generates specific queries based on the patient's underlying medical condition, medications and/or diagnoses (as reflected, for example, in start-up parameters for device 10 set at the time of installation or otherwise, e.g., by the health care provider). For example, based on such parameters, the processor can generate queries for a diabetic patient 20 regarding they took their prescribed insulin or whether they measured their fasting blood sugar, etc. In cases where treatment is rendered with assistance of a domestic or other care-giving partner, the queries can be directed to that person's perceptions of the patient's mental health and well being, etc., instead of or in addition to the patient's own perceptions.

The queries can be presented to the patient before, during and/or after the selected treatment session(s). See steps 44, 46. Preferably, in the case of pre- or post-treatment queries, they are generated sufficiently close in time (e.g., within an hour of treatment and, more preferably, within ½ hour of treatment and, still, more preferably within 10 minutes of treatment) to assure that the answers reflect the patient's state at the time of the treatment session.

In some embodiments, however, the processor 14 does not generate the queries in connection with selected treatment sessions per se. Rather, it generates the queries at a predetermined time, at a time selected ad hoc by the patient, or otherwise, on a daily, bi-daily, weekly, biweekly basis, or otherwise, regardless of treatment time. In such embodiments, the queries can nonetheless be directed to the patient's state in connection with the most recent treatment session(s) or otherwise.

Queries generated by the processor 14 are presented to the patient (and/or, for example, his/her domestic or other care-giving partner) via a liquid crystal display (LCD) 16 or other output device. Responses are input via keyboard or other input device 18. In the discussion that follows, the terms "patient query," "queries presented to patient," and the like, refer to the foregoing queries—regardless of whether they are presented to the patient directly or to his/her domestic or other care-giving partner. Likewise, the terms "response to query," "query responses," and the like, refer to responses to such queries—regardless of whether they are input by the patient directly or by his/her domestic or other care-giving partner.

In connection with at least selected treatment sessions—and, preferably, in connection with each treatment session—processor 14 acquires physiometric readings from sensors 28, operational readings from sensors 30, alerts (including incidence and duration information) from monitoring logic 32, and so forth. See step 48.

The communications logic (e.g., network interface 20) operates under control of the processor 14 to transmit query responses to the digital data processing system 24, along with readings from sensors 28, 30 and alerts from monitoring logic 32, for consideration by health care provider 22. See step 50. In the illustrated embodiment, those responses are transmitted e.g., at or around the time of completion of each treatment session, though, they can be transmitted at regular intervals (e.g., daily, weekly and so forth), e.g., when the device 10, network 26 and/or data processing system 24 is otherwise amenable to such transfer.

Alternatively, or in addition, the processor can store the query responses for each treatment session, along with readings from sensors 28, 30 and alerts from monitoring logic 32, to storage device 34, e.g., retaining the responses while awaiting transfer to the care provider. Indeed, in the case of such devices with removeable media, the patient 20 can bring that with him/her to monthly evaluation sessions at the hospital, dialysis clinic or other center, for uploading to digital data processing system 24 and consideration by health care provider 22.

Health care provider 22 utilizes the information transferred from device 10 for on-going diagnosis and treatment of the patient (both on acute and chronic bases), as well as for decision support, monitoring treatment compliance, facilitating regulatory compliance, billing, and so forth. See step 52. Thus, for example, the health care provider can initiate printing or other reporting of some or all of the transferred information for the patient's medical record or flow sheet, for patient billing, and so forth. Alternatively, or in addition, such printing and/or reporting can be initiated by analysis/reporting module 24A. Likewise, the health care provider and/or module 24A can print or otherwise report all or selected portions of the transferred information to support reimbursement requests and/or refilling of prescriptions for medications (such as EPO) provided to the patient as part of the treatment regimen. This can include, for example, reporting drugs taken by the patient in connection with treatment, including, for example, when those drugs were taken and in what amounts. The foregoing will, among other things, ensure that the provider has sufficient documentation to prove use, for example, of EPO and other renal-related pharmaceuticals (Vitamin D analogues, iron preparations etc) in connection with treatment of the patient 20. The printing/reporting of this will also allow for notification or even adjustment of billing for these drugs.

To that end, analysis/reporting module 24A can analyze the information transmitted by device 10, including, correlating response queries, sensor readings and alerts transmitted by device 10 and/or data in the patient's 20 electronic medical record and database with (i) each other, (ii) prior responses, readings, conditions, alerts from the device and/or other information for the patient (e.g., from medical records), (iii) expected responses, readings, conditions and/or alerts, e.g., based on empirical, normative or other standards, and/or (iv) so forth, in order to facilitate the health care provider's understanding of individual or multiple treatment sessions (e.g., over week-, month-, three month-periods, and so forth) and, more generally, in on-going patient diagnosis and treatment (both on acute and chronic bases), decision support, monitoring treatment compliance, facilitating regulatory compliance, billing, and so forth. See step 54.

By way of non-limiting example, the module 24A can correlate response queries, sensor readings and alerts transmitted by device 10 with one another to identify discrepancies, e.g., between response queries and physiometric sensor readings (e.g., patient reports "feeling fine," yet sensors suggest high fever), between operational and/or physiometric sensor readings (e.g., operational readings show numerous treatment sessions, yet, physiometric readings suggest decline in patient condition), and so forth. The module 24A can also correlate response queries, sensor readings and alerts transmitted by device 10 with historical such data transmitted by that device for the same patient, e.g., to discern whether the patient is improving or falling out of compliance with a treatment regime. The module 24A can also correlate response queries, sensor readings and alerts transmitted by device 10 with empirical or normative standards, e.g., established for patients of similar demographics, by health care provider, treatment center, by the insurer, by government agencies, and so forth. Module 24A can, additionally, analyze the transmitted data to identify additional alarm conditions or data patterns (e.g., based on ad hoc or other input from the physician, nurse or other health care provider).

In addition to performing the foregoing analyses, module 24A can identify trends occurring over time in the results of those analyses and/or in the underlying data received from device 10, facilitating not only identification of chronic or long-term conditions. For example, the module can identify trends in the patient's responses to questions directed to general emotional status and can correlate those trends with objective or other data (e.g., from the patient's electronic medical record) and/or perform trend analysis that, for example, provides an early indication of burn-out and allow for a timely intervention.

Moreover, the module 24A can identify patterns and frequencies of alarms, alerts, treatment information, patient symptoms and/or responses which represent deviations from the patient, health care provider and/or treatment facility norms and indicate potential problems or inefficiencies for evaluation and correction. The number, frequency and pattern of machine alarms, alerts, the time required to clear an alarm and vital sign information (blood pressure and pulse measurements) can provide significant information about individual patients clinical condition and/or changes in their medical condition. It also provides information about care delivery issues during both home hemodialysis, peritoneal dialysis and/or in-center hemodialysis. In this latter regard, for the example, the module 24A can provide the foregoing correlations not only for a given patient, but also for a treatment facility, e.g., comparing statistics for query responses, sensor readings, and/or alerts for multiple patients of a given facility with those of other facilities and/or standards. The module 24A can generate reports or other documentation with the outcome(s) of those comparisons, e.g., in support of billing, regulatory compliance, and so forth. Thus, paralleling an advantage discussed above, the module 24A helps ensure that treatment facilities are doing as expected.

Illustrated analysis/reporting module 24A can report the information transmitted by device 10 and/or results of the foregoing analyses for use by the health care provider in providing on-going patient diagnosis and treatment (both on acute and chronic bases), decision support, monitoring treatment compliance, facilitating regulatory compliance, billing, and so forth. Moreover, module 24A can trigger an immediate alert (e.g., in the form of e-mail, text message or otherwise) to a physician, nurse or other health care provider and/or generate a printout/report allowing an assessment of the patient's prescription and/or other medical comorbidites and diagnoses.

In some embodiments, the processor 14 is adapted to perform some or all of the analyzis and reporting functions described above in connection with module 24A. The results of those analyses can be transmitted to digital data processor 24 and/or can form the basis of immediate reporting alerts, e.g., to the patient and/or the physician, nurse or other health care provider. Thus, for example, such alerts can be generated if user starts to performs unusual steps during in setup or treatment, e.g, failing to perform disinfection, performing operations out of order, attempting to improperly increase ultrafiltration setting, offering bizarre subjective responses indicating illness, distress and/or incoherence. In some embodiment, when the processor 14 detects such conditions, it stops or prevents further treatment, e.g., in addition to signalling an alert.

FIGS. 3A-3B depict examples of reports of the type generated by module 24A (and/or processor 14 providing like functionality) correlating alarm (or other) information transmitted from device 10 with clinical information. More particularly, FIG. 3A depicts an example of a chart of the type generated by module 24A plotting the total number of alarms per treatment session vs date for a given patient over multiple treatment sessions, here, illustrated as running between September 29 and November 12. The circled regions of the plots identify total alarm counts of interest, e.g., values running above an upper control limit ("UCL") or below a lower control limit ("LCL"), as well as other alarm counts of interest, e.g., as determined in accord with standard statistical control principles (or otherwise). Those counts may results from mistakes in the procedure executed by the patients, abnormal physiological conditions resulting from patient illness, erroneous operation of device 10 or otherwise.

Although the illustrated plot is for total alarm counts, the module 24A (and/or processor 14 providing like functionality) can provide like charts for specific alarms, groups of alarms and/or other values contained within the information transmitted from device 10. Moreover, although the illustrated plot is for an individual patient, the module 24A (and/or processor 14 providing like functionality) can provide like charts per treatment facility, per health care provider, or otherwise. Likewise, although the date axis in the drawing is by date, the module 24A (and/or processor 14 providing like functionality) can provide like charts by week, bi-week, month, quarter, and so forth.

FIG. 3B likewise depicts an example chart of the type generated by module 24A similar to that shown in FIG. 3A, though, plotting a moving range. As above, the circles regions indicate values of interest. And, although the illustrated plot is for a moving range of total alarm counts, the module 24A (and/or processor 14 providing like functionality) can provide like charts for moving ranges of specific alarm counts, of groups of alarms and/or of other values contained within the information transmitted from device 10. Moreover, although the illustrated plot is for an individual patient, the module 24A (and/or processor 14 providing like functionality) can provide like charts per treatment facility, per health care provider, or otherwise. Likewise, although the date axis in the drawing is by date, the module 24A (and/or processor 14 providing like functionality) can provide like charts by week, bi-week, month, quarter, and so forth.

With reference to FIGS. 3A-3B, module 24A can generate circles or indications of the sort shown to identify values of interest in the illustrated plots, or can rely on the physician, nurse or other health care provider, himself or herself, to discern the problematic readings. Where the module 24A generates those circles or other indications, they can be based on standard statistical control principles or otherwise.

Module 24A can also generate patient and facility reports, as well as tabular "report cards" of the type shown in FIG. 4, by way of non-limiting example. That report lists, by patient, minimums, maximums, averages or other representative indications of the alarms, sensor readings or other data received from device 10 (here, indicated by abbreviations "Air", "AP", "BF", and so forth, along the top row of the chart). Also included on the illustrated report are comments by the health care provider, although, patient query responses, text messages (of the type described below) can be provided instead or in addition. The report can also provide totals for the identified patients, standards-based values, and comparisons therebetween, all as shown, by way of example, in the final three rows of the illustrated report.

The illustrated report includes colorations to identify readings or other values requiring physician, nurse or other health care provider attention. As above, module 24A can provide such coloration or indications on the generated reports, or can rely on the physician, nurse or other health care provider, himself or herself, to discern the problematic readings.

Analysis/reporting module 24A may generate the reports depicted in FIGS. 3-4 for printing or display, e.g., on LCD or other output device 24B. As well, these may be displayed on the liquid crystal display (LCD) or other output device 16 of device 10 in instances where it is deployed for access by the physician, nurse or other health care provider (e.g, when the device 10 is deployed at a hospital, dialysis clinic or other site).

Advantages of the analysis and reporting of query responses, sensor readings and alerts transmitted by device 10 and/or data in the patient's 20 electronic medical record as described herein and shown, by way of example, in FIGS. 3-4 are that it readily permits the physician, nurse or other health care provider to identify patients requiring medical attention, further training, counseling or other support. By way of further example, by reporting total number of alarms and time required to clear them, module 24A can be used to determine whether proper and efficient care is being delivered to the patient 20, and so forth.

This is advantageous over current practice, wherein clinicians respond to individual alarms and alerts but are not presented with patterns for individual treatments and for multiple treatment sessions that provide clinical context or normative references. This has heretofore prevented utilization of HHD-provided data to identify individual patient problems or issues with facility function or care delivery. This system will correct this gap and allow the full use of this additional and important information for care delivery and patient and facility oversight.

Messaging

In addition to the features discussed above, the aforementioned communications logic of device 10 can transmit text or other messages input by the patient via keyboard or other input device 18 to the health care provider. See steps 56, 58. The messages can be, for example, questions by the patient regarding his or her immediate or long-term treatment. They may be so-called "instant" messages that are transmitted in real-time (e.g., as the patient is entering them) to the digital data processing system 24 for presentation to care provider 22 and/or they can be queued for later transfer by the communications logic, e.g., along with the transfer query responses, sensor readings and alerts for each session. Though typically entered by the patient at the end of a treatment session, the keyboard or other input device 18 can accept a message from the patient (and the communications logic can transmit it) at any time the device 10 is operational.

The communications logic can, likewise, accept messages transmitted from the health care provider 22 via digital data processor 24. See step 60. Those messages, which may be, for example, responses to the patient's questions, suggestions on treatment, words of encouragement, and so forth, can be routed to processor 14 to LCD or other output device 16 for presentation to the patient. See step 62.

Although the communications logic can transmit text and other messages of the type just described between device 10 and digital data processor 24 via the same network 26 as is used for transfer of query responses, sensor readings and alerts for the treatment sessions, that communications logic can use other network media instead or in addition. Thus, for example, the communications logic can utilize the cellular phone network to transmit such messages (e.g., in the form of SMS messages or otherwise), while using an IP network such as the Internet to transfer the query responses, sensor readings and alerts for the treatment sessions. By way of further example, the communications logic can transmit such messages to a central monitoring system at digital processor 24, which then forwards them, e.g., via regular email, to a care delivery coordinator.

Described herein are systems and methods meeting the objects set forth above, among others. Advantages of the system and methods are, among others, that they allow care providers to readily monitor and document (or otherwise report on) the patient's treatment and response, providing alerts or other warnings when those are not proceeding as expected. It will be appreciated that the embodiments described here are merely examples of the invention and that other embodiments, incorporating modifications on those shown here, fall within the scope of the invention. Thus, by way of non-limiting example, in some embodiments, digital data processor 24 is co-located with device 10, e.g., in a dialysis clinic. In view of the foregoing:

We claim:

1. A health care delivery device comprising:
   A. medical treatment apparatus having one or more sensors that take biometric readings of a patient receiving medical treatment,
   B. an output device that presents information or other output for the patient,
   C. an input device that accepts information or other input in response to a query, and
   D. a processor that is coupled to the medical treatment apparatus and that generates subjective queries in connection with treatment of the patient thereby, the processor being coupled to the output device for presentation of those subjective queries for the patient and being coupled to the input device for accepting responses to those subjective queries, the processor comprising an analysis module that correlates the patient's responses and the biometric readings so as to monitor at least one of the treatment of the patient and operation of the medical treatment apparatus, and
   E. wherein the subjective queries include one or more of the patient's mental health and well being, quality of life, degrees of pain, and views on success of therapy.

2. The health device of claim 1, wherein the medical treatment apparatus comprises dialysis equipment.

3. The health device of claim 2, wherein the dialysis equipment comprises equipment for any of hemodialysis and peritoneal dialysis.

4. The health device of claim 1, adapted for treatment of the patient in a patient's home or other location remote from a dialysis treatment center.

5. The health device of claim 1, comprising communication functionality that transmits messages, input by the patient via the input device, to a remote care provider.

6. The health device of claim 5, the communication functionality accepts messages transmitted from a remote care provider and that presents those messages on the output device.

7. The health device of claim 6, wherein the messages are text messages.

8. A health care delivery system comprising:
   A. a digital data processing system,
   B. a health care delivery device disposed remotely from the digital data processing system, the health care delivery device being coupled for at least occasional communication with the digital data processing system and including
      i. medical treatment apparatus having one or more sensors that sense operating conditions of the medical treatment apparatus as the patient receives medical treatment therefrom,
      ii. an output device that presents information or other output for a patient,
      iii. an input device that accepts information or other input in response to a query,
      iv. a processor that is coupled to the medical treatment apparatus and that generates subjective queries in connection with treatment of the patient thereby, the processor being coupled to the output device for presentation of those subjective queries for the patient and being coupled to the input device for accepting responses to those subjective queries, the processor comprising an analysis module that correlates the patient's responses and the operating conditions of the medical treatment apparatus so as to monitor at least one of the treatment of the patient and operation of the medical treatment apparatus, and
      v. communication functionality that transmits one or more of the responses to the digital data processing system, and
   C. wherein the subjective queries include at least one of the following: patient's mental health and well being, quality of life, degrees of pain, and views on success of therapy.

9. A method of health care delivery comprising:
   A. delivering medical treatment to a patient via a medical treatment apparatus,
   B. subjectively querying the patient via a health care treatment device associated with the medical treatment apparatus, wherein the step of subjectively querying the patient includes querying the patient about at least one of the following: patient's mental health and well being, quality of life, degrees of pain, and views on success of therapy,
   C. accepting responses to those subjective queries,
   D. correlating the responses to those subjective queries with operating conditions of the medical treatment apparatus so as to monitor at least one of the treatment of the patient and operation of the medical treatment apparatus.

10. The method of claim 9, comprising transmitting messages, input by the patient, to a remote care provider.

11. The method of claim 10, comprising accepting messages transmitted from the remote care provider and presenting them for the patient.

12. The method of claim 11, wherein the messages are text messages.

13. A method of health care delivery comprising:
    A. delivering medical treatment to a patient via a medical treatment apparatus,
    B. subjectively querying the patient via a health care treatment device associated with the medical treatment apparatus, wherein the step of subjectively querying the patient includes querying the patient about at least one of the following: patient's mental health and well being, quality of life, degrees of pain, and views on success of therapy,
    C. accepting responses to those subjective queries,
    D. sensing physiometric characteristics of the patient and operating conditions of any of the health care treatment device and the medical treatment apparatus in connection with treatment by the medical treatment apparatus, E. correlating the responses to those subjective queries with at least one of the physiometric conditions of the patient and the operating conditions of any of the health care treatment device and medical treatment apparatus so as to monitor at least one of the treatment of the patient and operation of the medical treatment apparatus.

14. The method of claim 13, further comprising utilizing one or more of the patient responses, physiometric characteristics, and operating conditions received from the health care delivery device for any of diagnostics and billing.

15. A health care delivery device comprising:
A. medical treatment apparatus,
B. an input device that accept patient responses to one or more subjective queries,
C. sensors that sense (i) physiometric characteristics of the patient in connection with treatment by the medical treatment apparatus, and (ii) operating conditions of any of the health device and the medical treatment apparatus,
D. a processor that is coupled to the medical treatment apparatus and that
  (i) correlates the patient responses to one or more subjective queries with one or more of the physiometric characteristics, operating conditions received from the health care delivery device, another patient response, prior information received from the health care delivery device and/or from the patient's records, and one or more standards so as to monitor the treatment of the patient, and
  (ii) signals an alert on determining that the patient is not doing as expected,
E. wherein the subjective queries include at least one of the following: patient's mental health and well being, quality of life, degrees of pain, and views on success of therapy.

16. A health care delivery system comprising:
A. a health care delivery device including
  i. medical treatment apparatus,
  ii. an input device that accept patient responses to one or more subjective queries,
  iii. sensors that sense (a) physiometric characteristics of the patient in connection with treatment by the medical treatment apparatus, and (b) operating conditions of any of the health device and the medical treatment apparatus,
B. functionality that transmits one or more of the patient responses, physiometric characteristics and operating conditions a remote digital data processor,
C. the remote digital data processor
  (i) correlating one or more of the patient responses to the one or more subjective queries with any of physiometric characteristics, operating conditions received from the health care delivery device, another of the patient responses, prior information received from the health care delivery device and/or from the patient's records, and one or more standards, and
  (ii) any of generating a report and signaling an alert on determining that the patient is not doing as expected,
D. wherein the subjective queries include at least one of the following: patient's mental health and well being, quality of life, degrees of pain, and views on success of therapy.

17. The health care delivery system of claim 16, wherein the remote digital data processor (i) correlates any of patient responses, physiometric characteristics, and operating conditions received from a plurality of health care delivery device with any of (a) one another, (b) prior information received from the health care delivery devices and/or from patient records, (c) one or more standards, and (ii) any of generates a report and signals an alert on determining that a treatment facility is not doing as expected.

* * * * *